US 8,634,608 B2

(12) United States Patent
Frinking et al.

(10) Patent No.: US 8,634,608 B2
(45) Date of Patent: Jan. 21, 2014

(54) INSTANTANEOUS VISUALIZATION OF CONTRAST AGENT CONCENTRATION IN IMAGING APPLICATIONS

(75) Inventors: Peter Frinking, Genéve (CH); Nicolas Rognin, Genéve (CH); Marcel Arditi, Genéve (CH)

(73) Assignee: Bracco Suisse S.A., Manno (CH)

( * ) Notice: Subject to any disclaimer, the term of this patent is extended or adjusted under 35 U.S.C. 154(b) by 867 days.

(21) Appl. No.: 12/084,934

(22) PCT Filed: Nov. 10, 2006

(86) PCT No.: PCT/EP2006/068337
§ 371 (c)(1),
(2), (4) Date: Aug. 21, 2009

(87) PCT Pub. No.: WO2007/054561
PCT Pub. Date: May 18, 2007

(65) Prior Publication Data
US 2009/0324030 A1    Dec. 31, 2009

(30) Foreign Application Priority Data

Nov. 10, 2005 (EP) .................................. 05110597
Dec. 19, 2005 (EP) .................................. 05112379

(51) Int. Cl.
*G06K 9/00*    (2006.01)

(52) U.S. Cl.
USPC .......................................................... 382/128

(58) Field of Classification Search
USPC ........... 382/117, 128–131; 424/9.52; 600/458
See application file for complete search history.

(56) References Cited

U.S. PATENT DOCUMENTS

| 2002/0004634 A1* | 1/2002 | Greppi et al. .................. 600/458 |
| 2005/0249391 A1* | 11/2005 | Kimmel et al. ............... 382/128 |
| 2008/0008657 A1* | 1/2008 | Bussat et al. ................. 424/9.52 |

FOREIGN PATENT DOCUMENTS

| EP | A-0458745 A1 | 11/1991 |
| EP | A-0554213 A1 | 8/1993 |

(Continued)

OTHER PUBLICATIONS

Arditi M et al. ("Preliminary Study in Differential Contrat Echography" Ultrasound in Medicine and Biology, vol. 23, No. 8, pp. 1185-1194, (1997).*

(Continued)

*Primary Examiner* — Gerald J. O'Connor
*Assistant Examiner* — Edward Winston, III
(74) *Attorney, Agent, or Firm* — Graybeal Jackson LLP; Kevin D. Jablonski

(57) ABSTRACT

An embodiment of a system is proposed for imaging a body part including a tissue, the body part being perfused with a contrast agent. The system includes means for providing a sequence of original images offering a digital representation over time of the body-part, each original image including a plurality of original values each one indicative of a response to an interrogation signal of a corresponding location of the body-part possibly including the contrast agent with a contribution of the tissue substantially reduced. The system further includes means for generating an overlaid image for each one of a set of selected original images, for each one of a set of selected locations the overlaid image including an overlaid value consisting of a) a linearized value derived from the corresponding original value to be substantially proportional to a concentration of the contrast agent in the selected location when the linearized value reaches a predefined threshold, or otherwise b) a compressed value depending non-linearly on the corresponding response to the interrogation signal; and means for displaying the overlaid images in succession.

19 Claims, 7 Drawing Sheets

(56) References Cited

FOREIGN PATENT DOCUMENTS

| WO | WO-A-91/15244 | 10/1991 | | |
|----|----|----|----|----|
| WO | WO-A-94/09829 | 5/1994 | | |
| WO | WO-A-95/16467 | 6/1995 | | |
| WO | WO 2004/110279 A | 12/2004 | | |
| WO | WO 2004110279 A1 * | 12/2004 | ............... | A61B 8/06 |
| WO | WO 2007/054544 A1 | 5/2007 | | |

OTHER PUBLICATIONS

Handbook of Medical Imaging, Processing and Analysis (pp. 368-371, Chapter 23-> Section 3: "Quantitative Evaluation of Flow Motion" Bankman I. N. Editor; Academic Press), (2000).*
PCT International Search Report for International Application No. PCT/EP2006/068337, European Patent Office, May 2, 2007.
Marcel Arditi, Thomas Brenier and Michel Schneider, "Preliminary Study in Differential Contrast Echography", Ultrasound in Medicine and Biology, New York NY, US, vol. 23, No. 8, 1997,pp. 1185-1194, XP000764798.
Isaac N. Bankman Editor: "Chapter 23, Section 3: Quantitative Evaluation of Flow Motion". Handbook of Medical Imaging, Processing and Analysis, 2000, pp. 368-371, XP002382/95.
Toledo E., Lodato JA, Decara JM, Collins KA, Bednarz JE, Lang RM, Mor-Avi V; "Echocardiographic Detection of Stress-Induced Myocardial Ischemia Using Quantitative Analysis of Contrast-Enhanced Parametric Perfusion Images"; Computers in Cardiology, 2004; University of Chicago, Chicago, IL, USA Sep. 19-22, 2004, Piscataway, NJ, USA, IEEE, Sep. 19, 2004, pp. 233-236 XP010814035.
Paul A. Dayton, David Pearson, Jarrod Clark, Scott Simon, Patricia Schumann, Reena Zutshi, Terry Matsunaga, Katherine W. Ferrara, "Ultrasonic Enhancement of $\alpha\_v\beta\_3$ Expressing-Cells With Targeted Contrast Agents", 2003 IEEE Ultrasonic Symposium, pp. 540-543.
Patrick Rafter, Patrick Phillips, Mani A. Vannan, (2004) Elsevier Inc.,"Imaging technologies and techniques"; Cardiology Clinics; 22:181-197.
International Preliminary Report on Patentability mailed May 14, 2008 for International Application No. PCT/EP2006/068337, filed Nov. 10, 2006 for "Instantaneous Visualization of Contrast Agent Concentration in Imaging Applications," Peter Frinking et al., 9 pages.
Written Opinion mailed May 10, 2008 for International Application No. PCT/EP20061068337, filed Nov. 10, 2006 for "Instantaneous Visualization of Contrast Agent Concentration in Imaging Applications," Peter Frinking et al., 8 pages.

* cited by examiner

INSTANTANEOUS VISUALIZATION OF CONTRAST AGENT CONCENTRATION IN IMAGING APPLICATIONS

PRIORITY CLAIM

This application claims priority from PCT/EP2006/068337, published in English, filed Nov. 10, 2006, based on European patent Application No. 05110597.1, filed Nov. 10, 2005; this application also claims priority from European Application No. 05112379.2, filed Dec. 19, 2005, which are incorporated herein by reference.

TECHNICAL FIELD

An embodiment of the present invention relates to the medical imaging field. More specifically, an embodiment of the present invention relates to contrast agent imaging applications.

BACKGROUND

In the field of equipments for medical applications, imaging techniques are well-established for analyzing a body-part of a patient in a substantially non-invasive manner; for example, the imaging may be based on the recording of an echo signal that results from the application of ultrasound waves to the body-part. For this purpose, a contrast agent (for example, consisting of a suspension of phospholipid-stabilized gas-filled microbubbles in ultrasound applications) is typically administered to the patient; the contrast agent acts as an efficient (ultrasound) reflector, so that it enhances the visualization of blood in a vascular system within the body-part where it is present. Particularly, this technique is commonly exploited for the assessment of blood perfusion; indeed, as the contrast agent flows at the same velocity as the blood in the patient, its tracking provides information about the perfusion of the blood in the body-part under analysis.

Typically, the flow of the contrast agent is monitored by imaging the body-part during the perfusion process. More in detail, each image is defined by a matrix of pixel values indicative of the amplitude of the echo signal originating from corresponding portions of the body-part. For this purpose, the echo signal is usually compressed so as to adjust its amplitude to the smaller dynamic range that is commonly supported by video monitors. In order to obtain images with well-balanced contrast, the process always involves a non-linear compression; the operation is commonly based on a transfer function of the logarithmic type (and it is then referred to as log-compression).

Generally, in order to facilitate the tracking of the contrast agent, a contribution of any tissues of the body-part is at first reduced in the echo signal. This result may be achieved by acquiring the echo signal in a contrast-specific imaging mode. One example of such contrast-specific imaging is achieved by pulse inversion techniques. Other examples of contrast-specific imaging are achieved by power modulation techniques or by combinations of pulse inversion and power modulation techniques. Yet another example of contrast-specific imaging is disclosed in XP000764798 Arditi M. et al. "Preliminary Study in Differential Contrast Echography" Ultrasound in Medicine and Biology, Vol. 23, No. 8, pp. 1185-1194 1997, Elsevier, which is incorporated by reference. For this purpose, the cited document proposes processing the echo signal in two channels, whose signals are then subtracted; the processed signal so obtained is typically displayed in a linear gray-scale (i.e., with gray-levels proportional to the amplitude of the processed signal). In a specific implementation, the same processed signal is superimposed over an (unprocessed) log-compressed image.

In any case, the amplitude of either the video signal (i.e., the one obtained by compressing the amplitude of the echo signal) or of the contrast signal (i.e., the raw echo signal obtained as described in the cited document or by any other known contrast-specific imaging technique) is not in direct proportion to the local concentration of the contrast agent. As a matter of fact, only the power of the echo signal (i.e., the echo-power signal) exhibits a direct proportionality with the local concentration of the contrast agent.

With reference in particular to the video signal, as small differences in the echo signal (for example, with a ratio of 1.7 to 2.5, i.e., $20 \cdot \log_{10}(1.7) = 5$ dB to $20 \cdot \log_{10}(2.5) = 8$ dB) may be totally masked in the resulting compressed images, blood flow distributions with subtle variations or opacification heterogeneities (due to perfusion deficits) may thus be difficult to identify and can be easily overlooked. This hinders the detection of perfusion abnormalities, typically indicative of pathological conditions.

In any case, the resulting images strongly depend on the specific log-compression that is implemented by each type of equipment. Moreover, this process introduces subjectivity due to the setting of the log-compression according to different operator preferences. Therefore, the results obtained cannot be compared among operators using different equipments or settings.

On the other hand, a quantitative assessment of the perfusion process is provided by parametric analysis techniques. In this case, the video signal is preferably linearized so as to make its amplitude directly proportional to the local concentration of the contrast agent in the corresponding portions of the body-part. For this purpose, an inverse log-compression function is applied to the video signal, and the result so obtained is squared (so as to provide a signal in direct proportion to the local power of the original echo signal). The change over time of the linearized signal for each single pixel (or group of adjacent pixels) is fitted by a mathematical function. The mathematical function may then be used to calculate different perfusion parameters, which are indicative of corresponding haemodynamic and morphological characteristics of the corresponding portion of the body-part (such as the relative blood volume, its velocity, flow, and the like).

The result of the above-described analysis may also be represented graphically by means of a so-called parametric image (or map). The parametric image is built by assigning the respective values of a selected perfusion parameter to each pixel. Typically, different ranges of values of the perfusion parameter are coded with corresponding colors; the pixel values so obtained are then overlaid on one of the original images. In this way, the parametric image shows the spatial distribution of the perfusion parameter throughout the body-part under analysis.

However, although the parametric images may facilitate the identification of possible portions of the body-part that are abnormally perfused, they simply provide a static representation of the perfusion parameters. Therefore, the parametric images do not allow a direct visual perception of the perfusion process, which is normally provided by the playback of the original sequence of images.

In any case, the parametric analysis techniques usually require time-consuming processing of the information that was recorded; therefore, the obtained results are only available off-line (i.e., not in real-time during the perfusion process).

SUMMARY

An embodiment of the invention is based on the idea of dynamically representing linearized signals.

Particularly, an embodiment of the invention proposes a system for imaging a body part including a tissue, while said body part is perfused with a contrast agent. The system includes means (such as an ultrasound scanner) for providing a sequence of original images (offering a digital representation over time of the body-part). Each original image includes a plurality of original values; each original value is indicative of a response to an interrogation signal (such as an echo signal resulting from insonifying ultrasound pulses) of a corresponding location of the body-part—which possibly includes the contrast agent—with a contribution of the tissue that is substantially reduced (for example, being acquired in a contrast-specific imaging mode). The system further includes means for generating an overlaid image for each one of a set of selected original images (such as all of them or a subset ensuing from a temporal sub-sampling). This result is achieved by operating on a set of selected locations, which set may include all the locations of the original images or a portion thereof (for example, in a region or interest, or ROI). For each selected location, the overlaid image includes an overlaid value. The overlaid value consists of a linearized value, derived from the corresponding original value, substantially proportional to a concentration of the contrast agent in the selected location when the linearized signal reaches a predefined threshold (for example, when said linearized value exceeds the threshold); otherwise (i.e., when the linearized value is below the threshold), the overlaid value consists of a compressed value that depends non-linearly on the corresponding response to the interrogation signal. Means is further provided for displaying the overlaid images in succession.

Typically, the linearized value is proportional to a local echo power.

Moreover, the compressed value commonly depends on the echo signal according to a logarithmic law.

In an embodiment of the invention, the threshold is higher than a corresponding residual contribution of the tissue.

Generally, the sequence of original images is obtained by applying one or more insonifying ultrasound pulses, recording the corresponding radio-frequency echo signals (raw signals), processing them to substantially reduce the contribution of the tissue, and then generating the desired original images.

Advantageously, the pixels outside the ROI are assigned the corresponding compressed values.

Generally, the compressed value is derived from the original value as well.

An embodiment of the proposed solution is commonly applied starting from compressed values; in this case, the overlaid image is obtained by replacing each compressed value within the ROI with its linearized value when it is necessary (with the linearized value that is calculated from the compressed value by applying an inverse log-compression function and squaring the obtained result).

For this purpose, in an embodiment of the invention a linearized image is generated by linearizing the compressed values for the pixels within the ROI; the linearized values so obtained are then compared with the threshold.

As a further enhancement, the linearized images are spatially sub-sampled according to their estimated resolution (for example, based on the size of speckle grains that typically occur in ultrasound imaging).

In an embodiment of the invention, the linearized values are represented according to a color lookup table (distinct from the one of the compressed values).

An embodiment of the proposed solution is particularly advantageous when the overlaid images are displayed substantially in real-time during the acquisition of the corresponding original images.

Another embodiment of the present invention proposes a corresponding method for imaging a body part perfused with a contrast agent.

A further embodiment of the present invention proposes a computer program for performing the method.

BRIEF DESCRIPTION OF THE DRAWINGS

Features and advantages of one or more embodiments of the invention, will be best understood with reference to the following detailed description, given purely by way of a non-restrictive indication, to be read in conjunction with the accompanying drawings, in which.

DETAILED DESCRIPTION

Figure 1:
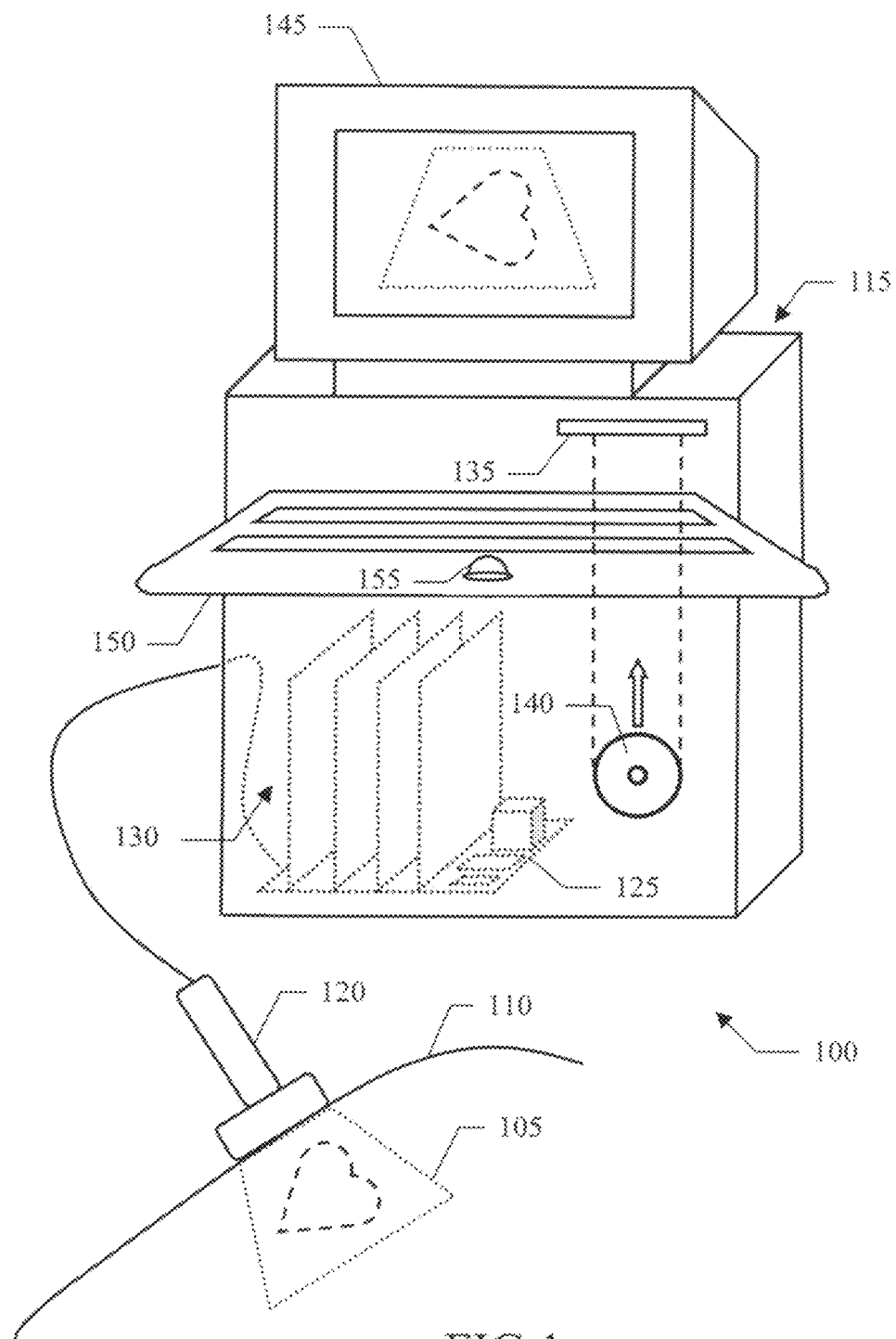
FIG. 1 is a pictorial representation of an ultrasound scanner in which a solution according to an embodiment of the invention is applicable.

With reference in particular to FIG. 1, a medical imaging system consisting of an ultrasound scanner 100 is illustrated; the scanner 100 is used to analyze a body-part 105 of a patient 110, and especially to assess its blood perfusion (for example, for diagnostic purposes).

Particularly, the ultrasound scanner 100 includes a central unit 115 with a hand-held transmit-receive imaging probe 120 (such as of the array type). The imaging probe 120 transmits ultrasound waves consisting of a sequence of insonifying ultrasound pulses (for example, having a center frequency between 2 and 10 MHz), and receives a (raw) radio-frequency (RF) echo signal resulting from the reflection of the ultrasound pulses; for this purpose, the imaging probe 120 is provided with a transmit/receive multiplexer, which allows using the imaging probe 120 in the pulse-echo mode.

The central unit 115 houses a motherboard 125, on which the electronic circuits controlling operation of the ultrasound scanner 100 (such as a microprocessor, a working memory and a hard-disk drive) are mounted. Moreover, one or more daughter boards (denoted as a whole with 130) are plugged on the motherboard 125; the daughter boards 130 provide the electronic circuits for driving the imaging probe 120 and for processing the received echo signal. The ultrasound scanner 100 can also be equipped with a drive 135 for reading removable disks 140 (such as floppy-disks). A monitor 145 displays images relating to the analysis process that is in progress. Operation of the ultrasound scanner 100 is controlled by means of a keyboard 150, which is connected to the central unit 115 in a conventional manner; preferably, the keyboard is provided with a trackball 155 that is used to manipulate the position of a pointer (not shown in the FIG.) on a screen of the monitor 145.

In order to assess the blood perfusion in the body-part 105, an Ultrasound Contrast Agent (UCA) is administered to the patient 110; the contrast agent is preferably provided by an intravenous injection, either as a continuous infusion (e.g., by means of an infusion pump) or as a bolus (typically by hand with a syringe).

Suitable contrast agents include suspensions of gas bubbles in a liquid carrier; typically, the gas bubbles have diameters on the order of 0.1-5 μm, so as to allow them to pass through the capillary bed of the patient. The gas bubbles are generally stabilized by entraining or encapsulating the gas or a precursor thereof into a variety of systems, including emulsifiers, oils, thickeners, sugars, proteins or polymers; stabilized gas bubbles are referred to as gas-filled microvesicles. The microvesicles include gas bubbles dispersed in an aqueous medium and bound at the gas/liquid interface by a very thin envelope involving a surfactant, i.e., an amphiphilic material (also known in this case as microbubbles). Alternatively, the microvesicles include suspensions in which the gas bubbles are surrounded by a solid material envelope formed of lipids or of natural/synthetic polymers (also known as microballoons or microcapsules). Another kind of contrast agent includes suspensions of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). A commercial ultrasound contrast agent comprising gas-filled microvesicles is SonoVue® by Bracco International BV.

The imaging probe 120 is placed in contact with the skin of the patient 110 in the area of the body-part 105 to be analyzed. The echo signal that is recorded in response to ultrasound pulses over time results from the superimposition of a contribution due to the tissues of the body-part 105 and a contribution due to the contrast agent. The ultrasound scanner 100 operates in a contrast-specific imaging mode so as to substantially reduce the (linear) contribution of the tissues in the echo signal with respect to the (non-linear) contribution of the contrast agent; examples of contrast-specific imaging modes include harmonic imaging (HI), pulse inversion (PI), power modulation (PM) and contrast pulse sequencing (CPS) techniques, as described, for example, in "Rafter et al., Imaging technologies and techniques, Cardiology Clinics 22 (2004), pp. 181-197" (the entire disclosure of which is herewith incorporated by reference). Generally, the reduction of the contribution of the tissues in the (processed) echo signal with respect to the original (unprocessed) echo signal is defined by the ratio of their amplitudes (in dB); in an embodiment, the reduction is at least 40 dB, for example at least 50 dB, and for further example at least 60 dB. Therefore, in the normal practice, a residual contribution of the tissue is always present in the processed echo signal. This residual contribution may be used to display information on the anatomy of the body-part under evaluation. In some embodiments, the contribution of the tissue may, however, be completely removed. Thus, only the contribution of the contrast agent is present in the processed echo signal and no information about the anatomy of the body part under analysis is available in it. In this case, possible information about the anatomy of the body part under analysis may be derived, if desired, from standard non contrast-specific echo signals, as illustrated in the following of the description.

The resulting echo signal is then converted into a sequence of digital images (or frames) that represent the body-part 105 at corresponding successive acquisition instants (for example, with an imaging rate of 10-30 images per second). Each image is defined by a bitmap comprised of a matrix (for example, with 512 rows and 512 columns) of values for respective visualizing elements, i.e., basic picture elements (pixels) or basic volume elements (voxels); each pixel (or voxel) corresponds to a location consisting of a small portion of the body-part 105. Typically, the pixel value is represented by a gray-scale level (for example, of 8 bits) that defines the brightness of the pixel; the pixel value increases according to the intensity of the corresponding echo signal (representing the acoustical response at the pixel location), from 0 (black) to 255 (white).

During the above-mentioned process, the echo signal is subjected to a non-linear compression to improve the visualization quality of the images. Indeed, the amplitude of the echo signal has a large dynamic range, defined as the ratio between the minimum and maximum usable values of its (voltage) amplitude; for example, the dynamic range of the echo signal amplitude ($DR_E$) can readily exceed 10,000 (i.e., $20 \cdot \log_{10}(10,000) = 80$ dB). However, the dynamic range that an observer can generally perceive on the monitor 145 is less than 30 dB. Therefore, in order to allow visual perception of all the useful information contained in the echo signal, it is necessary to amplify the echo signal in a non-linear manner, so as to enhance the lower amplitude echo signals. This makes it possible to obtain images with well-balanced contrast, which convey useful anatomical information about the body-part 105 under analysis.

The desired result is usually achieved by compressing the echo signal through a transfer function of the logarithmic type. Each manufacturer of the scanner 100 has a peculiar approach to the implementation of this log-compression. For example, a video signal to be displayed on the monitor 145 may be set equal to a compressed signal obtained by applying the following transfer function:

$$A_V = A_C = \frac{MAX_V}{LC/20} \cdot \log_{10}\left(\frac{A_E}{MAX_E} \cdot 10^{\frac{LC}{20}}\right), \quad (0.1)$$

where $A_E$ is the amplitude of the echo signal, $MAX_E$ is the maximum allowable amplitude of the echo signal, LC is a parameter defining the desired compression factor (in dB), $A_V$ is the amplitude of the video signal, $MAX_V$ is the maximum allowable amplitude of the video signal, and $A_C$ is the amplitude of the compressed signal.

The transfer function (0.1) was verified experimentally by using a phantom material mimicking a tissue (such as a polyurethane gel with solid scatterers embedded therein). For a given value of the compression factor LC, a series of images was acquired by varying the gain setting of the scanner (displayed in dB), which defined the amplitude of the echo signal, so as to cover its whole dynamic range $DR_E$. The images were analyzed off-line by measuring the pixel values in a very small area contained within a single speckle grain.

Figure 2:
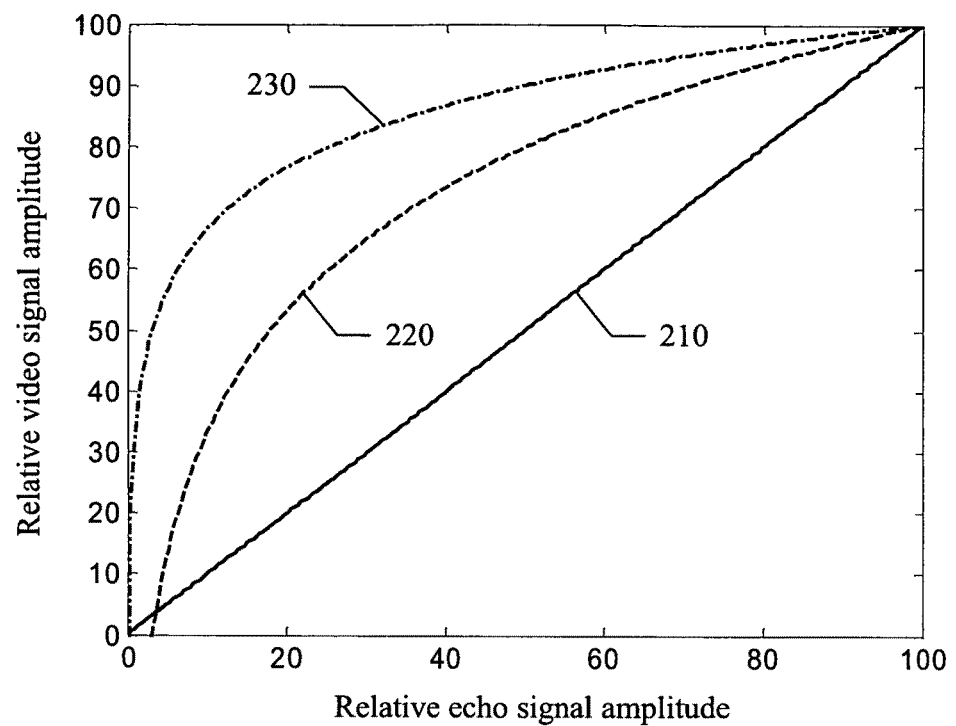
FIG. 2 is an explanatory diagram illustrating the effect of the log-compression.

The effect of the log-compression due to the application of the transfer function (0.1) is illustrated schematically in FIG. 2. Particularly, this FIG. provides a diagram that plots the amplitude of the video signal (on the axis of the ordinates) against the amplitude of the echo signal (on the axis of the abscissas), both of them expressed in relative terms from 0 to 100 (with the relative video signal amplitude equal to $$\frac{A_V}{MAX_V} \cdot 100$$

and the relative echo signal amplitude equal to $$\frac{A_E}{MAX_E} \cdot 100 ).$$

As can be seen, a curve 210 (in solid line) indicates a linear relationship (with the video signal proportional to the echo signal), which would be obtained by linearly mapping the echo signal into the video signal (without any log-compression). In contrast, a curve 220 (in dashed line) and a curve 230 (in dash-dotted line) represent non-linear relationships resulting from the application of the transfer function (0.1) with the compression factor LC equal to 30 dB and 60 dB, respectively.

It is evident that the log-compression actually amplifies the echo signal in a non-linear manner, so as to enhance lower values thereof. Particularly, the video signal is always zero for values of the echo signal below a minimum value $MIN_E$ given by the intersection of the curves 220,230 with the axis of the abscissas (i.e., $A_V$=0):

$$MIN_E = \frac{MAX_E}{10^{\frac{LC}{20}}}.$$

For values of the echo signal above this minimum value $MIN_E$, the video signal takes a significant value even for a very small increase thereof. However, the desired result implies a loss of proportionally between the video signal and the echo signal; this effect is more apparent for higher values of the compression factor LC (i.e., in the curve 230 with respect to the curve 220).

Linearization of the video signal is instead important for deriving correct functional information relating to the blood perfusion in the body-part under analysis. As used hereinafter, the term linearization indicates any processing that makes the amplitude of the video signal (i.e., the pixel values) directly proportional to the local concentration of the contrast agent in the corresponding pixel locations. This linearized signal provides a direct representation of the (relative) local blood volume in the respective portions of the body-part (since the contrast agent concentration is related, i.e., proportional, to the blood volume). As a consequence, the linearized signal allows a correct assessment of the blood perfusion in the body-part.

This result is obtained by calculating a local power of the echo signal. When the echo signal is directly accessible, this is simply obtained by squaring its amplitude:

$$A_L = (A_E)^2, \quad (0.2)$$

where $A_L$ is the amplitude of the linearized signal; in this case, the linearized signal extends from a minimum value $MIN_L$=0 to a maximum value $MAX_L$=$(MAX_E)^2$. However, in most practical situations the video signal only is available; in this case, the linearization is obtained by applying an inverse log-compression (to reverse its effect) and then squaring the result so obtained, as described in WO-A-2004/110279 (the entire disclosures of which is herein incorporated by reference). For example, when the log-compression is defined by the transfer function (0.1), the linearized signal is calculated by means of the following inverse function:

$$A_L = \left[ MAX_E \cdot 10^{\frac{LC \cdot (A_V - MAX_V)}{20 \cdot MAX_V}} \right]^2. \quad (0.3)$$

In this case, the linearized signal amplitude extends from a minimum value $MIN_L$ to a maximum value $MAX_L$ that are given by:

$$MIN_L = \left[ MAX_E \cdot 10^{\frac{LC \cdot (0 - MAX_V)}{20 \cdot MAX_V}} \right]^2$$

$$= \left[ MAX_E \cdot 10^{\frac{-LC \cdot MAX_V}{20 \cdot MAX_V}} \right]^2$$

$$= \left( \frac{MAX_E}{10^{\frac{LC}{20}}} \right)^2$$

and $$MAX_L = \left[ MAX_E \cdot 10^{\frac{LC \cdot (MAX_V - MAX_V)}{20 \cdot MAX_V}} \right]^2$$

$$= (MAX_E)^2,$$

respectively.

Figure 3:
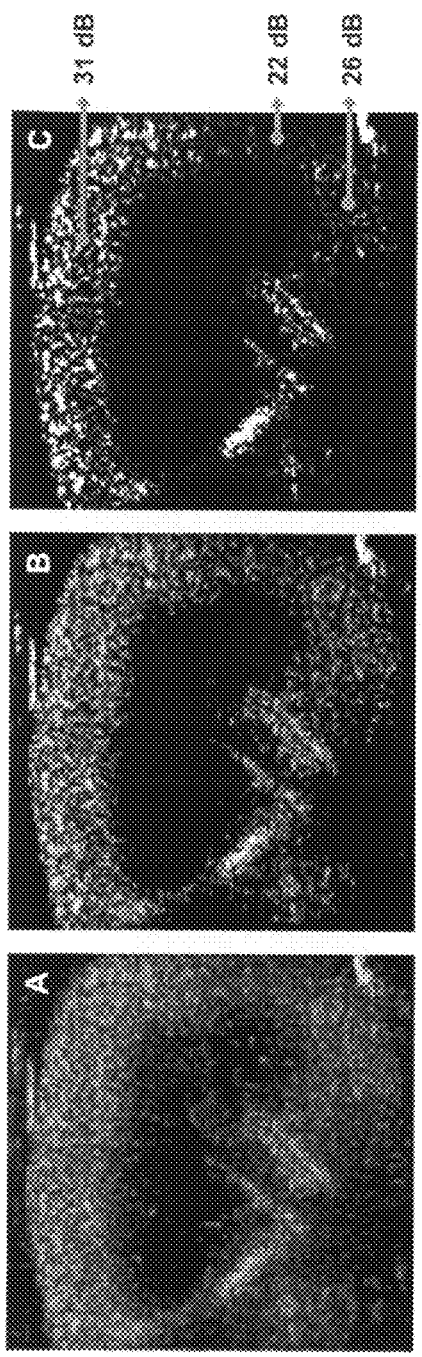
FIG. 3 shows exemplary applications of the log-compression and of the linearization.

Exemplary applications of the log-compression and of the linearization to an in-vivo analysis are illustrated in FIG. 3. For this purpose, three images were acquired of a rabbit kidney at the peak of the contrast agent concentration after a bolus injection. The images denoted with (A) and (B) were obtained by applying the log-compression based on the transfer function (0.1) with the compression factor LC equal to 83 dB and 40 dB, respectively; conversely, the image denoted with (C) was obtained by linearizing the video signal. It is evident from this FIG. that the appearance of the images strongly depends on the applied processing.

Particularly, the image (A) obtained with the higher compression factor LC provides a well-balanced representation of the body-part under analysis; in this case, the compressed image (A) shows an apparent uniform opacification of the whole kidney cortex. When the compression factor LC is lowered, as shown in the compressed image (B), the visualization quality is degraded to some extent; however, a slight opacification heterogeneity now appears in the area corresponding at 4 o'clock. Conversely, the linearization in the image (C) makes it evident that the opacification is heterogeneous; however, this result is achieved at the cost of a very poor representation of the body-part under analysis.

Particularly, the linearized image (C) now allows detecting that the upper part of the kidney cortex is bright and uniform, while its lower-right part is much less opacified. This conclusion was confirmed by standard off-line quantification analysis of the same image (C). For this purpose, the pixel values were measured in an upper region, a middle region and a lower region of the linearized image (C); those pixel values were then averaged in each region. As can be seen, the mean pixel values in the middle region (22 dB) and in the lower region (26 dB) were significant lower than the mean pixel value (31 dB) in the upper region. Assuming a uniform transducer sensitivity with depth, the corresponding differences (9 dB and 5 dB, respectively) are indicative of a reduced contrast agent concentration (since the linearized signal is proportional thereto); the associated deficit in the blood perfusion might signify a pathological state of this part of the kidney cortex.

A solution according to an embodiment of the present invention overlays the linearized image on the original compressed image for their simultaneous display. For this purpose, a ROI is selected. Each pixel inside the ROI is assigned a (linearized) value substantially proportional to the local echo power (i.e., proportional to the concentration of the contrast agent when present in the corresponding portions of the body-part under analysis) when this linearized value reaches a predefined threshold TH; the other pixels inside the ROI (which linearized values are below the threshold TH) and the pixels outside the ROI are displayed as in the original compressed image.

The proposed overlay representation ensures that the anatomical information about the body-part under analysis is not lost in the images shown on the monitor. At the same time, this allows identifying blood flow distributions with subtle variations, or opacification heterogeneities; therefore, the detection of perfusion abnormalities (typically indicative of pathological conditions) is strongly facilitated.

Moreover, the obtained results are less dependent on the type of equipment that is used; in any case, any subjectivity (due to the setting of the log-compression) is avoided. As a consequence, it is now possible to compare the results among operators using different equipments or settings.

An embodiment of the proposed solution thus provides an animated representation of the evolution over time of the concentration of the contrast agent (during the perfusion process).

It is emphasized that the desired result is available instantaneously, without the need of any time-consuming off-line analysis. Therefore, the obtained images may be displayed in real-time during the perfusion process. This allows making a first quick diagnosis about the location and the severity of possible pathologies; it may then be possible to decide immediately whether any further investigation is needed (and possibly which treatment procedure must be followed).

The threshold TH may set to be higher than a corresponding (reduced) contribution of the tissues in the linearized signal (i.e., higher than a linearized limit, which is obtained by linearizing an original limit of the contribution of the tissues in the echo signal). For this purpose, the threshold TH may be set to a predefined percentage of the maximum linearized signal; for example, the threshold TH may chosen in the range of 1-10%, for example in the range of 4-7%, such as equal to 5%, of the maximum linearized signal. In this way, the linearized values that are higher than the threshold TH represent the contrast agent only (when its concentration is significant). On the contrary, the compressed values for the other pixels—whose linearized values are below the threshold TH—represent the tissues only (with the possible addition of the contrast agent at very low concentration). As it may be appreciated by those skilled in the art, in those instances where the contribution of the tissue in the linearized signal can be substantially completely removed, the threshold TH may advantageously be set to zero.

The linearized images are scaled by an arbitrary gain factor and displayed according to a separate color lookup table. In this way, any differences in the echo signal are further emphasized.

Figure 4:
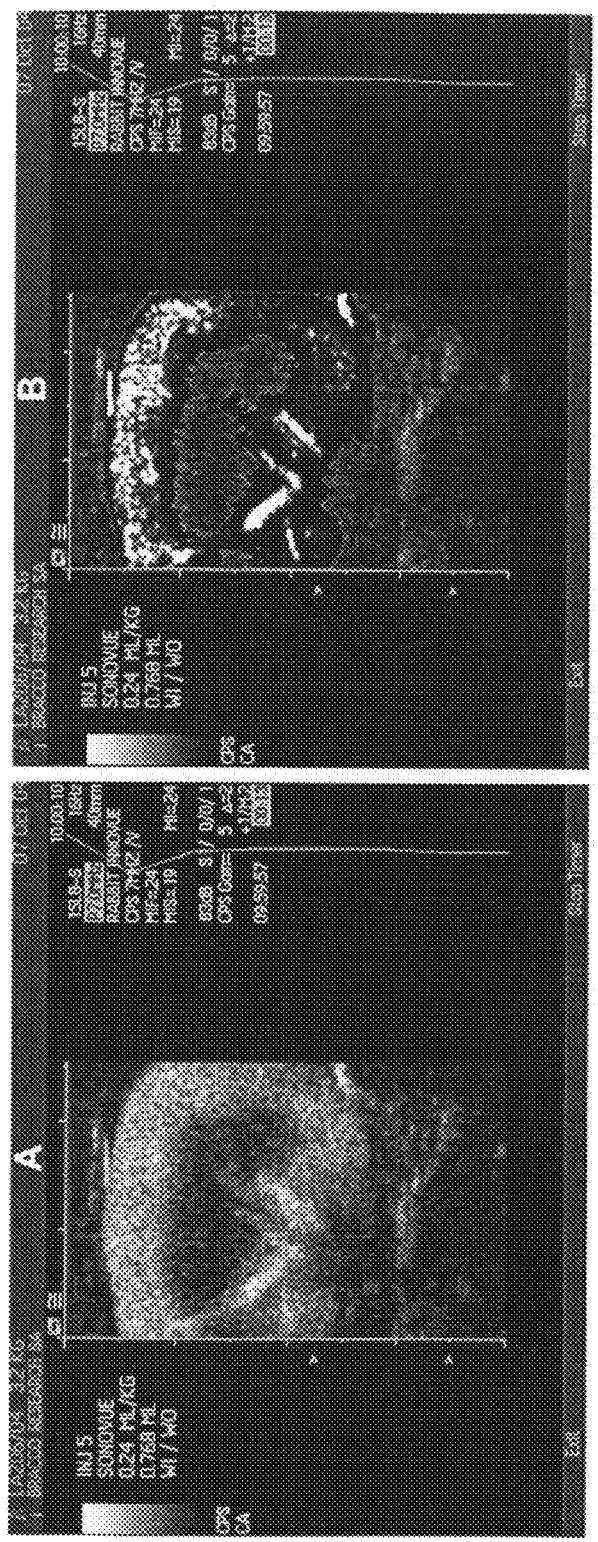
FIG. 4 shows an exemplary application of a solution according to an embodiment of the invention.

Moving now to FIG. 4, an exemplary application of an embodiment of the solution described above is illustrated using the same experimental data of FIG. 3. Particularly, the image on the left (A) corresponds to the compressed image denoted with the same reference in FIG. 3 (obtained with the higher compression factor LC). Conversely, the image on the right (B) is obtained from the image (A) by overlaying the corresponding linearized image on this compressed image according to a method based on an embodiment of the invention. The pixels displayed as in the linearized image are easily recognized (by their color coding) with respect to the pixels displayed as in the compressed image (i.e., the original grayscale levels). In this way, it is possible to identify a perfusion heterogeneity of the lower-right part of the kidney cortex immediately; at the same time, the obtained image provides a well-balanced representation of the body-part under analysis in the background.

Figure 5A:
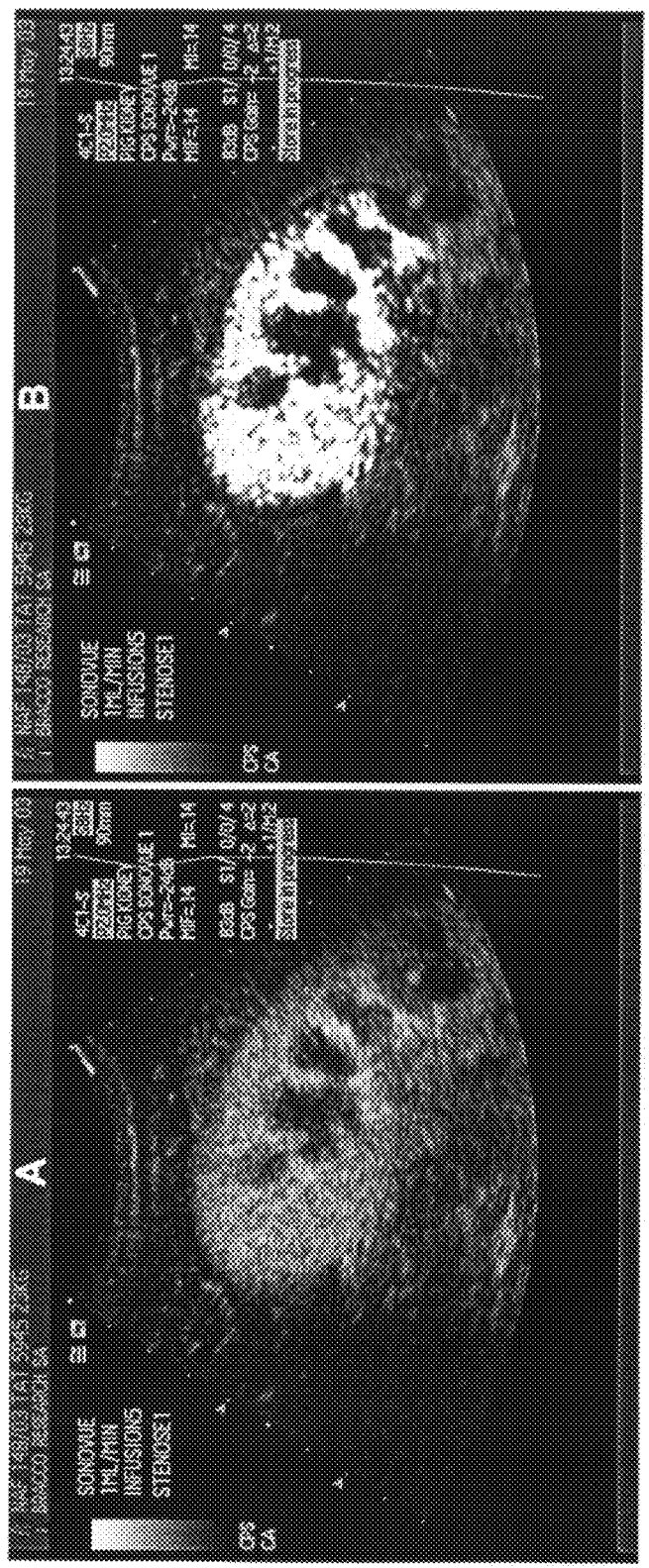
FIGS. 5a-5b show another exemplary application of a solution according to an embodiment of the invention.

Another exemplary application of the same solution is shown in FIG. 5a. In this case, an image (A) was acquired by applying a standard log-compression. The image (A) represents a pig kidney at the steady state of the contrast agent concentration during a continuous infusion of the contrast agent; a 30% stenosis was induced in the renal artery to create an abnormal perfusion in the kidney cortex. The image (A) shows a uniform opacification of the whole kidney cortex, so that the perfusion abnormality cannot be detected.

A corresponding image denoted with (B) was obtained by applying the above-described solution on a selected ROI, which is delimited by an elliptical region in the FIG. As a result, the pixels inside the ROI are displayed as in the linearized image or as in the compressed image (when the corresponding linearized value is strictly higher or lower than the threshold TH, respectively); conversely, the pixels outside the ROI are always displayed as in the compressed image. As can be seen, a suspect region is now clearly visible at the top of the kidney cortex (without adversely affecting the anatomical representation of the same body-part).

Figure 5B:
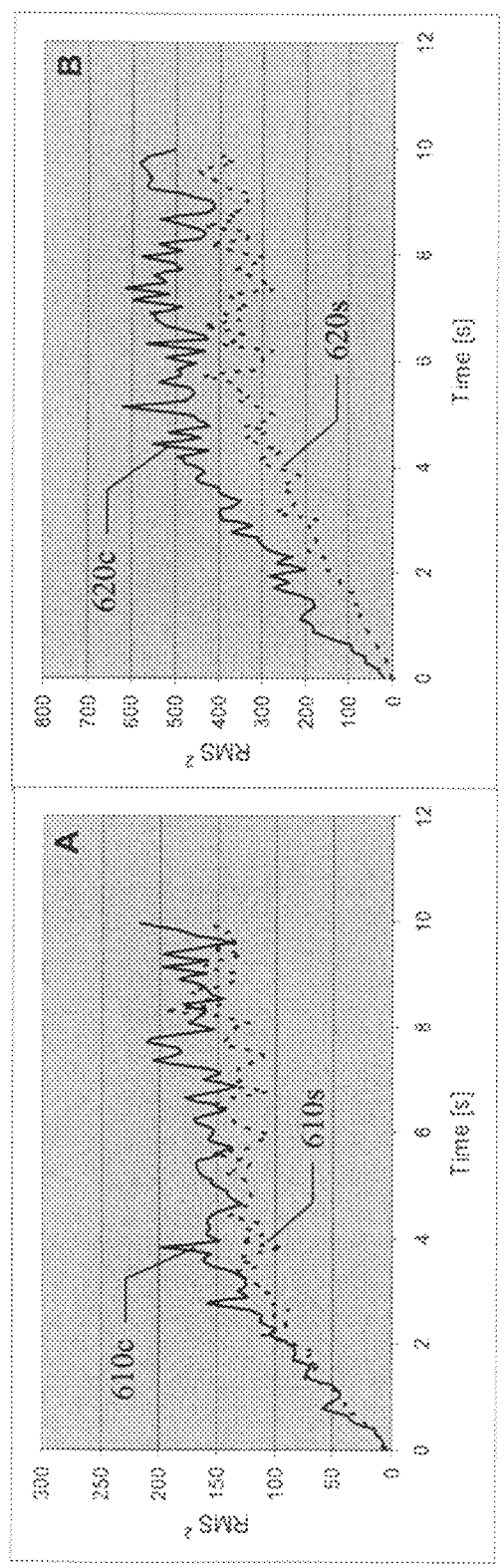

The location of that perfusion abnormality was confirmed by standard analysis of the kidney cortex by means of fluorescent micro-spheres. Moreover, off-line quantification analysis of the perfusion was performed on a sequence of images of the kidney cortex acquired with a destruction-replenishment technique; particularly, Squared Root-Mean-Square ($RMS^2$) values of the linearized video signal were calculated for the pixels in a ROI placed in the suspected region and in another ROI placed in a control region at its left (allegedly in a healthy condition). As shown in FIG. 5b, the diagram denoted with (A) plots the $RMS^2$ values over time for the suspected region (curve $610s$) and for the control region (curve $610c$) in a baseline condition before inducing the stenosis. As can be seen, the curves $610s$ and $610c$ are very similar. On the other hand, the diagram denoted with (B) plots the $RMS^2$ values over time for the same suspected region (curve $620s$) and for the same control region (curve $620c$) in the stenotic condition. In this case, the curve $620s$ of the suspected region clearly differs from the curve $620c$ of the control region, thereby confirming the correct location of the perfusion abnormality.

Figure 6:
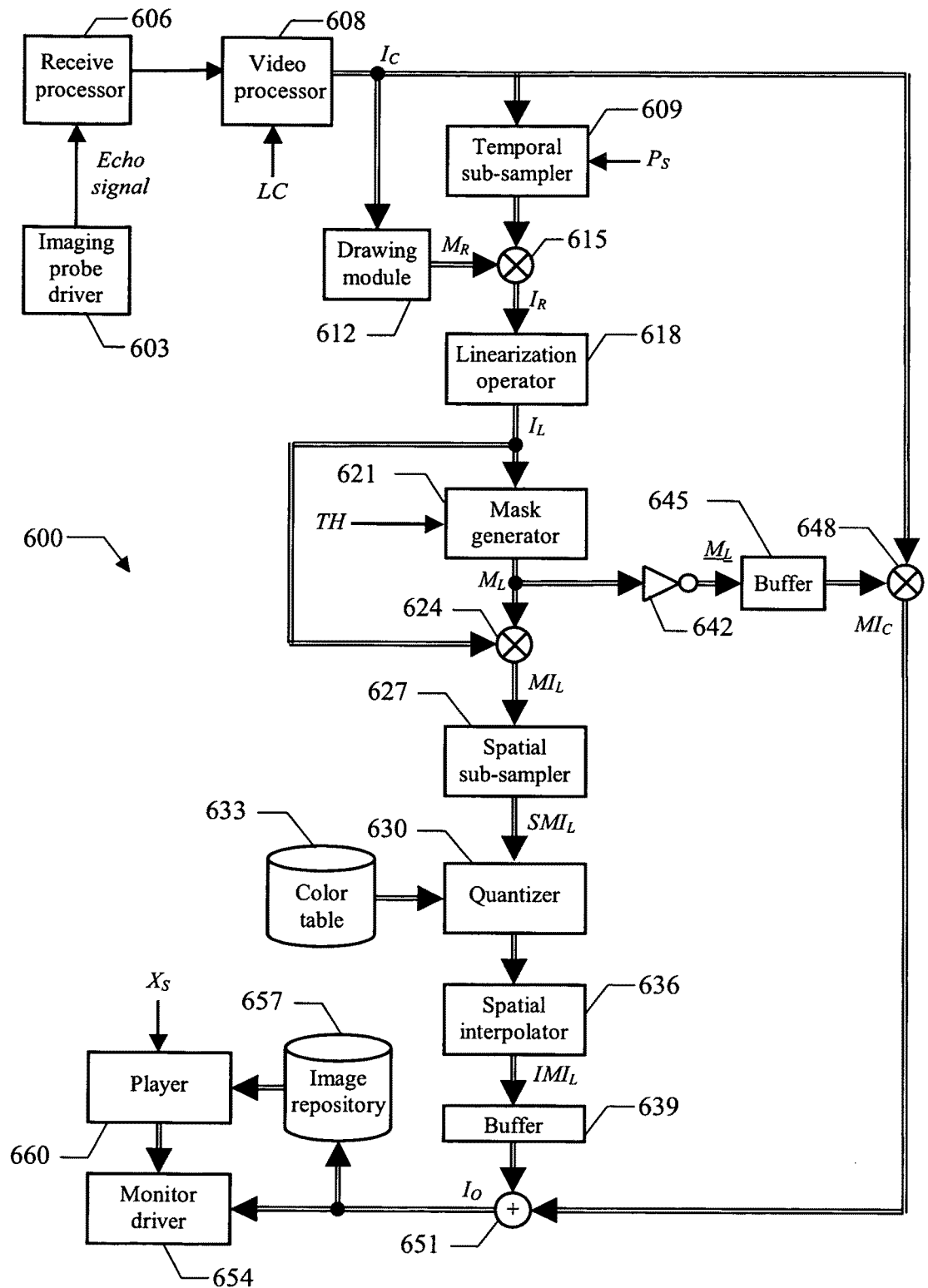
FIG. 6 depicts the main software and hardware components that can be used for practicing a solution according to an embodiment of the invention.

Moving now to FIG. 6, the main software and hardware components that may be used for practicing a solution according to an embodiment of the invention are denoted as a whole with the reference 600. The information (programs and data) is typically stored on the hard disk and loaded (at least partially) into the working memory when the programs are running, together with an operating system and other application programs (not shown in the FIG.). The programs are initially installed onto the hard disk, for example, from CD-ROM.

Particularly, a driver 603 controls the imaging probe (not shown in the FIG.); for example, the imaging probe driver 603 includes a transmit beam former and pulsers for generating the ultrasound pulses to be applied to the body-part under analysis. The corresponding (analog RF) echo signal that is received from said body-part is supplied to a receive processor 606. Typically, the receive processor 606 pre-amplifies the analog RF echo signal and applies a preliminary time-gain compensation (TGC); the analog RF echo signal is then converted into digital values by an Analog-to-Digital Converter (ADC), and combined into a focused signal through a receive beam former. The digital signal so obtained may be processed through further digital algorithms and other linear or non-linear signal conditioners (such as a post-beam-forming TGC). Particularly, the receive processor 606 applies a contrast-specific algorithm to suppress the contribution of the tissues (such as based on the above-mentioned HI, PI, PM or CPS techniques). The digital signal so processed is passed to a video processor 608, wherein it is demodulated, log-compressed, and scan-converted into a video format. The process results in the recording of a sequence of compressed images $I_C$. For this purpose, the video processor 608 receives as input the desired compression factor LC.

The compressed images $I_C$ are provided to a temporal sub-sampler 609, which also receives a sub-sampling parameter $P_S$ (for example, from 0 to 10). The temporal sub-sampler 609 outputs one compressed image $I_C$ out of every $P_S+1$; for this purpose, the temporal sub-sampler 609 lets a compressed image $I_C$ pass through and then skips the next $P_S$ ones. In most practical situations, the sub-sampling parameter Ps is set to 0 (so that every compressed image $I_C$ is taken into account); higher values of the sub-sampling parameter Ps are instead used to limit the number of compressed images $I_C$ to be processed (for example, when the ultrasound scanner works at ultra-high frame rates, such as 100-500 frames per second).

A drawing module 612 is used to predefine a ROI for the analysis process on the compressed images $I_C$ (from the video processor 608). The operation generates a reduction mask $M_R$, which consists of a matrix of binary values with the same size as the compressed images $I_C$ (i.e., M×N); the binary values inside the ROI are assigned the logic value 1, whereas the binary values outside the ROI are assigned the logic value 0. A multiplier operator 615 receives the (possibly temporally sub-sampled) compressed images $I_C$ from the temporal sub-sampler 609 and the reduction mask $M_R$ from the drawing module 612. The operator 615 multiplies each compressed image $I_C$ by the reduction mask $M_R$ pixel-by-pixel, so as to generate a corresponding sequence of reduced images $I_R$. As a result, the reduced images $I_R$ only include the pixel values of the compressed images $I_C$ that are inside the ROI (defined by the reduction mask $M_R$), while the other pixel values are reset to 0.

Each reduced image $I_R$ is provided to a linearization operator 618, which outputs a corresponding linearized image $I_L$. Particularly, the operator 618 linearizes the reduced image $I_R$ pixel-by-pixel, so as to make each pixel value of the linearized image $I_L$ directly proportional to the local echo power (i.e., proportional to the concentration of the contrast agent when present in the body part under analysis); in the example at issue, this result is achieved by applying the formula (0.3) to every pixel value of the reduced image $I_R$.

The linearized image $I_L$ is then passed to a mask generator 621, which is controlled by the threshold TH. The mask generator 621 creates a corresponding linearization mask $M_L$; the linearization mask $M_L$ is obtained from the linearized image $I_L$ by assigning (to each pixel) the logic value 1 if its value exceeds the threshold TH or the logic value 0 otherwise. A multiplier operator 624 receives the linearized image $I_L$ (from the linearization operator 618) and the linearization mask $M_L$ (from the mask generator 621). The operator 624 multiplies the linearized image $I_L$ by the linearization mask $M_L$ pixel-by-pixel, so as to generate a corresponding masked (linearized) image $MI_L$. As a result, the masked image $MI_L$ only includes the pixel values of the linearized image $I_L$ that exceed the threshold TH, while the other pixel values are reset to 0.

A spatial sub-sampler 627 receives the masked image $MI_L$ so obtained. The module 627 sub-samples the masked image $MI_L$ according to a factor based on the spatial frequency content of one of the compressed images Ic (for example, according to the size of speckle grains that typically occur in ultrasound imaging, for example, equivalent to 2-6 pixels). The spatial sub-sampling may comprise low-pass filtering followed by sub-sampling. The low-pass filtering has a cutoff frequency, which can be chosen as the highest frequency component containing significant energy in a selected one of the compressed images Ic (for example, determined by Fourier analysis). The sub-sampling is performed according to a factor that can be determined, for example, as a value resulting in a spatial sub-sampling frequency equal to twice the cutoff frequency. In this way, the masked image $MI_L$ is transformed into a corresponding sub-sampled masked image $SMI_L$; each value of the sub-sampled masked image $SMI_L$ thus represents a cell corresponding to a group of adjacent pixels in the masked image $MI_L$ (which cell has a size defined according to the above-mentioned spatial resolution). This allows smoothing any irregularity in the recorded information (for example, due to any misalignments of the compressed images $I_C$).

The (sub-sampled) masked image $SMI_L$ is then provided to a quantizer 630. The quantizer 630 is adapted to convert the cell values of the masked image $SMI_L$ into corresponding discrete values (for example, consisting of 64 or 128 levels that are uniformly distributed from 0 to the maximum video signal $MAX_V$), by possibly applying a gain factor. The quantizer 630 also accesses a color (look-up) table 633. The color table 633 associates all the possible levels with the representation of corresponding colors (that are preferably brighter as the levels increase); for example, each color is defined by an index for accessing a location within a palette containing its actual specification. The quantizer 630 replaces each cell value in the masked image $SMI_L$ with the corresponding color representation.

The masked image $SMI_L$ is provided to a spatial-interpolator 636. The spatial-interpolator 636 restores the full-size of the masked image $SMI_L$ corresponding to the size of the compressed images $I_C$ (i.e., M×N) by means of interpolation techniques (such as based on the nearest neighbor, bilinear, or bicubic technique). For this purpose, the value of each cell in the masked image $SMI_L$ is replicated for the corresponding group of pixels (nearest neighbor interpolation method) and optionally filtered spatially (such as using a low-pass 2D or 3D spatial filter). The operation generates a corresponding (interpolated) masked image $IMI_L$. The masked image $IMI_L$ is latched into a single-image buffer 639 (replacing its previous content). In this way, the masked image $IMI_L$ in the buffer 639 is updated whenever a new compressed image $I_C$ is output by the temporal sub-sampler 609, while it remains unchanged otherwise (so as to maintain the last calculated masked image $IMI_L$).

Concurrently, the linearization mask $M_L$ is also supplied from the mask generator 621 to an inverter 642, which generates a corresponding inverted (linearization) mask $\overline{M_L}$ (by exchanging the logic values 0 and 1). The inverted mask $\overline{M_L}$ is likewise latched into a single-image buffer 645 (replacing its previous content), so as to be always synchronized with the masked image $IMI_L$ in the buffer 639. A multiplier operator 648 receives the inverted mask $\underline{M_L}$ (latched in the buffer 645) and a current compressed image $\overline{I_C}$ (from the video processor 608). The operator 648 multiplies the compressed image Ic by the inverted mask $M_L$ pixel-by-pixel, so as to obtain a corresponding masked (compressed) image $\overline{MI_C}$. As a result, the masked image $MI_C$ includes the pixel values of the corresponding compressed image $I_C$ that are outside the ROI and below the threshold TH within the ROI, while the other pixel values within the ROI are reset to 0.

An adder operator 651 receives the masked image $IMI_L$ (latched in the buffer 639) and the masked image $MI_C$ (from the multiplier operator 648). The operator 651 adds the masked image $IMI_L$ and the masked image $MI_C$ pixel-by-pixel (correctly synchronized) so as to obtain an overlaid image Io. In this way, each pixel value of the overlaid image $I_O$ within the ROI is displayed as in the linearized image $I_L$ whenever that pixel value (in the same linearized image $I_L$) is larger than the threshold TH; the other pixel values within the ROI that are below the threshold TH and all the pixel values outside the ROI are instead displayed as in the compressed image Ic.

The overlaid image Io is passed to a monitor driver 654, which controls its visualization. The same operations described above are reiterated for each new compressed image $I_C$ that is recorded; as a result, the overlaid images Io are displayed in succession on the monitor of the ultrasound scanner in real-time; this means that the overlaid images Io are available substantially at the same time when the corresponding compressed images $I_C$ are acquired (or with a short delay, but in any case without the need to wait for the completion of their acquisition for starting the displaying).

In addition or in alternative, the sequence of overlaid images $I_O$ so obtained may also be saved into a repository 657. The repository 657 is accessed by a player 660; the player 660 also receives an index Xs, which is selected according to the desired reproduction speed of the overlaid images $I_O$; for example, the speed index Xs is set to 1 for a reproduction in real time, to a value lower than 1 for a reproduction in slow-motion or to a value higher than 1 for a reproduction in accelerated-motion. The player 660 extracts the overlaid images $I_O$ in succession from the repository 657. Each overlaid image $I_O$ is then passed to the monitor driver 654 for its playback (with a frame rate corresponding to the selected speed index Xs).

Modifications

Naturally, in order to satisfy local and specific requirements, a person skilled in the art may apply to the embodiments described above many modifications and alterations. Particularly, although the present invention has been described with a certain degree of particularity with reference to embodiment(s) thereof, it should be understood that various omissions, substitutions and changes in the form and details as well as other embodiments are possible; moreover, it is expressly intended that specific elements and/or method steps described in connection with any disclosed embodiment of the invention may be incorporated in any other embodiment as a general matter of design choice.

For example, similar considerations apply if the ultrasound scanner has a different structure or includes other units (such as with an imaging probe of the linear-, convex-, phased-, or matrix-array type). Likewise, an embodiment of the invention lends itself to be put into practice with equivalent contrast agents (even administrated in other ways, such as intra-arterial). In addition, an embodiment may be used in applications that do not relate to the perfusion assessment; a typical example is the detection and the quantification of the contrast agent that is immobilized on a specific biological target, as described in the co-pending application No. PCT/EP06/068305 of 9 Nov. 2006 (the entire disclosure of which is herein incorporated by reference).

Moreover, any other technique may be used to reduce the contribution of the tissues in the echo signal (for example, by applying the algorithm described in the above-cited document by Arditi at al.). It should also be noted that the proposed numerical examples for the reduction of the contribution of the tissues in the echo signal are not to be interpreted in a limitative manner; particularly, the complete removal of the contribution of the tissues from the echo signal is within the scope of the invention.

In any case, nothing prevents the application of the proposed processing to all the available images (without any temporal sub-sampling).

Naturally, the above-described transfer function defining the log-compression and the formulas for linearizing the available images are merely illustrative; similar considerations apply to different transfer functions of the logarithmic type, or more generally to any other non-linear compression.

Moreover, the numerical examples for the threshold TH should not be interpreted in a limitative manner; more generally, nothing prevents setting the threshold TH in other ways (even independently of the residual contribution of the tissues). In any case, a similar result may be achieved in a system based on negative images (wherein the pixel values decrease with the intensity of the echo signal) by using a different (maximum) threshold.

Although an embodiment of the invention has been specifically designed for ultrasound applications, nothing prevents its use in any other medical imaging application, such as based on Magnetic Resonance Imaging (MRI) or X-ray Computed Tomography (CT).

Alternatively, embodiments may also be applied in a system that consists of an ultrasound scanner and a distinct computer (or any equivalent data processing entity); in this case, the recorded information is transferred from the ultrasound scanner to the computer for its processing (for example, through the removable disk, a memory key, or a network connection).

According to an alternative embodiment, the pixel values outside the selected ROI may be reset to 0 (so that the portion of the overlaid image outside the ROI is black); however, the application of the proposed solution to the whole content of the compressed images is contemplated.

According to a different embodiment of the invention, the compressed values for the pixels inside the ROI whose linearized values are below the threshold TH, and for the pixels outside the ROI, may be obtained from any other signals. For example, the compressed values from signals obtained with a non contrast-specific imaging modality, such as fundamental B-mode imaging, may be advantageously employed. These values can be obtained, for instance, from the echo signals of the imaging probe driver. The values so obtained may thus be used as the compressed values in the overlaid images to represent, for instance, the anatomy of the body part under analysis. At the same time, the linearized values assigned to the pixels inside the ROI exceeding the threshold TH are obtained from signals wherein the contribution of the tissues has been reduced with respect to the one of the contrast agent. As previously mentioned, when the contribution of the tissues in the linearized signal is completely removed, the threshold TH may advantageously be set to zero.

Without departing from the principles of this disclosure, it is also possible to apply the thresholding to the compressed values (instead of the linearized values); in this case, the linearized values are only calculated for the compressed values that exceed the threshold. Moreover, when the (non-compressed) echo signal is accessible, the overlaid image may also be directly composed by linearizing each pixel value above the threshold or by compressing it otherwise.

In some embodiments, the linearized signal might be already available for other purposes (such as when parametric analysis techniques are implemented); in this case, it is possible to exploit the available information without any additional linearization operation.

Similar considerations apply if the linearized images are spatially sub-sampled with a different procedure (for example, according to a predefined sub-sampling factor), or if the spatial sub-sampling is performed beforehand or afterward; in any case, the application of an embodiment of the proposed solution at the pixel level (instead of at the level of groups of pixels defined by the above-mentioned spatial sub-sampling) is not excluded.

It should also be noted that the step of applying the gain factor on the linearized values may be replaced by applying a differently scaled color lookup table; in any case, a gray-scale representation of the linearized values is within the scope of an embodiment of the invention.

As described above, even if advantages of one or more embodiments of the present invention are more clearly perceived when the overlaid images are displayed in real-time, the application of the devised solution for analyzing the obtained results off-line is contemplated.

Similar considerations apply if the program (which may be used to implement one or more embodiments of the invention) is structured in a different way, or if additional modules or functions are provided; likewise, the memory structures may be of other types, or may be replaced with equivalent entities (not necessarily consisting of physical storage media). Moreover, one or more embodiments of the proposed solution lend themselves to be implemented with an equivalent method (having similar or additional steps, even in a different order). In any case, the program may take any form suitable to be used by or in connection with any data processing system, such as external or resident software, firmware, or microcode (either in object code or in source code). Moreover, the program may be provided on any computer-usable medium; the medium may be any element suitable to contain, store, communicate, propagate, or transfer the program. Examples of such medium are fixed disks (where the program can be pre-loaded), removable disks, tapes, cards, wires, fibers, wireless connections, networks, broadcast waves, and the like; for example, the medium may be of the electronic, magnetic, optical, electromagnetic, infrared, or semiconductor type.

In any case, an embodiment according to the present invention lends itself to be carried out with a hardware structure (for example, integrated in a chip of semiconductor material), or with a combination of software and hardware.

What is claimed is:

1. A system for imaging a body part including a tissue, the body part being perfused with a contrast agent, the system comprising: means for providing a sequence of original images offering a digital representation over time of the body part, each original image including a plurality of original values each one indicative of a response to an interrogation signal of a corresponding location of the body part possibly including the contrast agent with a contribution of the tissue being substantially reduced; means for generating an overlaid image for each one of a set of selected original images, for each one of a set of selected locations the overlaid image including an overlaid value having: a) a linearized value derived from the corresponding original value to be proportional to a concentration of the contrast agent in the selected location in response to the linearized value having reached a threshold, or b) a compressed value depending non-linearly on the corresponding response to the interrogation signal; and means for displaying the overlaid images in succession.

2. The system according to claim 1, wherein the linearized value is substantially proportional to a power of the corresponding response to the interrogation signal.

3. The system according to claim 1, wherein the compressed value depends on the corresponding response to the interrogation signal according to a substantially logarithmic law.

4. The system according to claim 1, wherein the threshold is higher than a corresponding limit of the reduced contribution of the tissue.

5. The system according to claim 1, wherein the means for providing the sequence of original images includes:
    means for applying at least one insonifying ultrasound pulse to the body-part;
    means for recording a corresponding radio-frequency echo signal in response to the at least one insonifying ultrasound pulse;
    means for processing the radio-frequency echo signal to substantially reduce the contribution of the tissue; and
    means for generating the sequence of original images from the processed echo signal.

6. The system according to claim 1, wherein for each non-selected location the overlaid value includes the compressed value.

7. The system according to claim 1, wherein each compressed value is derived from the corresponding original value.

8. The system according to claim 7, wherein each original value includes the compressed value, the compressed value depending on the corresponding response to the interrogation signal according to a non-linear compression function, and wherein the means for generating the overlaid image includes:
    means for replacing the compressed value of each selected location with the corresponding linearized value in response to the linearized value having reached the threshold, the linearized value being calculated by applying an inverse function of the compression function to the compressed value and squaring a result of the application of the inverse function.

9. The system according to claim 8, wherein the means for generating the overlaid image further includes:
    means for converting each selected original image into a linearized image by replacing the compressed value of each selected location with the corresponding linearized value; and
    means for comparing each linearized value in the linearized image with the threshold.

10. The system according to claim 9, wherein the means for generating the overlaid image further includes:
    means for applying a spatial sub-sampling to the linearized image according to an estimated resolution thereof.

11. The system according to claim 1, wherein the means for generating the overlaid image further includes:
    means for associating a plurality of predefined colors with corresponding ranges of the linearized values; and
    means for replacing each linearized value in the overlaid image with a representation of a corresponding color.

12. The system according to claim 1, wherein the means for displaying are adapted to display each overlaid image substantially in real-time with an acquisition instant of the corresponding selected original image.

13. A method for imaging a body part including a tissue, the body part being perfused with a contrast agent, the method comprising: providing a sequence of original images offering a digital representation over time of the body part, each original image including a plurality of original values each one indicative of a response to an interrogation signal of a corresponding location of the body part possibly including the contrast agent with a contribution of the tissue being substantially reduced; generating an overlaid image for each one of a set of selected original images, for each one of a set of selected locations the overlaid image including an overlaid value having: a) a linearized value derived from the corresponding original value to be proportional to a concentration of the contrast agent in the selected location in response to the linearized value having reached a threshold, or otherwise b) a compressed value depending non-linearly on the corresponding response to the interrogation signal; and displaying the overlaid images in succession.

14. An article of manufacture, comprising: a computer program product including a non-transitory computer-readable medium having stored thereon a computer program, wherein the computer program in response to being executed on a data processing system causes the system to perform imaging of a body part having a tissue and being perfused with a contrast agent, by: providing a sequence of original images offering a digital representation over time of the body part, each original image including a plurality of original values each one indicative of a response to an interrogation signal of a corresponding location of the body part possibly including the contrast agent with a contribution of the tissue being substantially reduced; generating an overlaid image for each one of a set of selected original images, for each one of a set of selected locations the overlaid image including an overlaid value having: a) a linearized value derived from the corresponding original value to be proportional to a concentration of the contrast agent in the selected location in response to the linearized value having reached a threshold, or otherwise b) a compressed value depending non-linearly on the corresponding response to the interrogation signal; and displaying the overlaid images in succession.

15. The system of claim 1, wherein said displaying is performed in real-time during a perfusion process.

16. The system of claim 1, wherein the concentration of the contrast agent is proportional to a power of an echo signal.

17. The method of claim 13, wherein said displaying is performed in real-time during a perfusion process.

18. The method of claim 13, wherein the concentration of the contrast agent is proportional to a power of an echo signal.

19. The article of manufacture of claim 14, wherein said displaying is performed in real-time during a perfusion process, and wherein the concentration of the contrast agent is proportional to a power of an echo signal.

* * * * *